United States Patent
Rest et al.

(10) Patent No.: US 7,588,912 B2
(45) Date of Patent: Sep. 15, 2009

(54) COMPOSITIONS AND METHODS FOR PREVENTING AND TREATING ANTHRAX DISEASES

(75) Inventors: Richard Rest, Rosemont, PA (US); Michael Karin, La Jolla, CA (US); Jin Mo Park, Charlestown, MA (US)

(73) Assignees: Regents of the University of California, Oakland, CA (US); Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 11/248,081

(22) Filed: Oct. 12, 2005

(65) Prior Publication Data

US 2006/0204525 A1    Sep. 14, 2006

Related U.S. Application Data

(60) Provisional application No. 60/617,936, filed on Oct. 12, 2004.

(51) Int. Cl.
    *C12Q 1/18*   (2006.01)
    *A61K 39/07*  (2006.01)
    *A61K 38/00*  (2006.01)

(52) U.S. Cl. ............... 435/32; 424/246.1; 514/2

(58) Field of Classification Search .......... None
    See application file for complete search history.

(56) References Cited

OTHER PUBLICATIONS

Moayeri M, Sheppla SH (2004) The role of anthrax toxin in pathogenesis. Current Opin Microbiol 7: 19-24.*
Moayeri M, Haines D, Young HA, Sheppla SH. (2003) *Bacillus anthracis* lethal toxin induces TNF-alpha-independent hypoxia-mediated toxicity in mice. J Clin Invest 112: pp. 670-682.*
Mourez M, Kane RS, Mogridge J, Metallo S, Deschatelets P, Sellman BR, Whitesides GM, Collier RJ (2001) Designing a polyvalent inhibitor of anthrax toxin. Nature Biotechnology 19: pp. 958-961.*
Kim SO, Ono K, Tobias PS, and Han J. (2003) Orphan nuclear receptor Nur77 is involved in caspase-independent macrophage cell death. J Exp Med 197: pp. 1441-1452.*
Ivins BE et al (1998) Comparative efficacy of experimental anthrax vaccine candidates against inhalation anthrax in rhesus macaques. Vaccine, vol. 16, No. 11/12, pp. 1141-1148.*
Ascenzi P et al (2002) Anthrax toxin: a tripartite lethal combination. FEBS Lett, vol. 531, pp. 384-388.*
Shannon JG et al (Jun. 2003) Characterization of anthrolysin O, the *Bacillus anthracis* cholesterol-dependent cytolysin. Infection and Immunity, vol. 71, No. 6, pp. 3183-3189.*
Popov et al, Biochemical and Biophysical Research Communications, 2002, vol. 293, pp. 349-355.*

* cited by examiner

*Primary Examiner*—Jon P Weber
*Assistant Examiner*—Laura Schuberg
(74) *Attorney, Agent, or Firm*—Caesar, Rivise, Bernstein, Cohen & Pokotilow, Ltd.

(57) ABSTRACT

Compounds, methods for identifying compounds and methods for using compounds which modulate interaction of lethal factor and anthrolysin O in the treatment and prevention of anthrax diseases are provided.

1 Claim, No Drawings

COMPOSITIONS AND METHODS FOR PREVENTING AND TREATING ANTHRAX DISEASES

This application claims the benefit of priority from U.S. Provisional Application Ser. No. 60/617,936 filed Oct. 12, 2004, which is herein incorporated by reference in its entirety.

This invention was supported in part by funds from the U.S. government (NIH Grant No. AI61712 and U54 AI57168). The U.S. government may therefore have certain rights in the invention.

INTRODUCTION

1. Field of the Invention

The interaction of lethal factor and anthrolysin O has now been identified as critical to macrophage apoptosis occurring in anthrax diseases. The present invention relates to methods for identifying compounds which modulate the interaction of lethal factor and anthrolysin O and compositions and methods for use of such compositions comprising a compound which modulates the interaction of lethal factor and anthrolysin O in preventing and treating anthrax diseases.

2. Background of the Invention

*Bacillus anthracis* is a highly virulent Gram-positive *bacillus* that is the causative agent of different forms of anthrax (1). At lease part of the extreme virulence of *B. anthracis* is due to production of several exotoxins or virulence factors: lethal factor (LF), edema factor (EF) and protective antigen (PA) (2, 3). While PA binds to receptors expressed on the surface of host cells and allows cellular entry of LF and EF (4, 5), LF and EF possess essential enzymatic activities that alter host cell signaling (6-8). LF is a metalloproteinase with unique specificity to MAP kinase (MAPK) kinases (MKKs), which severs the C-terminal MKK catalytic domain from the N-terminal regulatory domain (8, 9). This cleavage results in dismantling of MAPK activation cascades (8), whose normal function depends on interaction of the N-terminal MKK regulatory domain with upstream MKK kinases (MEKKs or MAP3Ks) and downstream MAPKs (10). We found that incubation with low amounts of *B. anthracis* lethal toxin (LT), a hetero-oligomer of PA and LF (2,3), renders macrophages sensitive to lipopolysaccharide (LPS)-induced apoptosis by preventing activation of p38 mitogen-activated protein kinase (MAPK) pathway (11). This response, which depends on the proteolytic cleavage of MKK6 by LF, can be mimicked by the use of low-molecular weight p38 inhibitors, such as SB202190 (11). More recently, we demonstrated that infection of BMDMs with live *B. anthracis* (Sterne strain) also results in extensive apoptosis, that depends on signaling from the LPS-responsive Toll-like receptor TLR4 that activates the proapoptotic double-stranded (ds) RNA-dependent protein kinase PKR (12).

*B. anthracis*, however, is a Gram-positive bacterium which does not produce LPS and thus it remained to be identified which component of *B. anthracis* activates TLR4 and induces apoptosis of macrophages exposed to LF.

It has now been found that anthrolysin O (ALO), a cholesterol-dependent cytolysin (CDC) secreted by *B. anthracis* (13), acts together with LT to induce macrophage apoptosis.

SUMMARY OF THE INVENTION

An object of the present invention is to provide a composition for treating or preventing anthrax diseases which comprises a compound which modulates the interaction of lethal factor and anthrolysin O.

Another object of the present invention is to provide a method for identifying compounds for treatment and prevention of anthrax diseases which comprises assessing the ability of a compound to modulate the interaction of lethal factor and anthrolysin O.

Another object of the present invention is to provide a method for treating or preventing anthrax diseases in a host which comprises administering to the host a compound which modulates the interaction of lethal factor and anthrolysin O.

DETAILED DESCRIPTION OF THE INVENTION

Several lines of circumstantial evidence have suggested that *B. anthracis* interacts with host immune cells through TLRs: *B. anthracis* infection elicits a cytokine response in both mice and cultured macrophages (27, 28), and causes macrophage apoptosis in a manner dependent on TLR4 signaling (12). Nonetheless, the identity of the *B. anthracis* component that is responsible for inducing cytokine and apoptotic responses in macrophages was not hitherto known. It was previously reported that macrophages treated with very low doses of LT produce TNF-α and IL-1β (29), suggesting a role for LT in cytokine response. Unlike TLR agonists, however, LT induces IL-1β production by causing the release of mature IL-1β derived from a pre-synthesized pool of IL-1β precursor rather than activating IL-1β gene expression (30, 31). This effect is reminiscent of the *Shigella* IpaB and *Salmonella* SipB invasins, which cause IL-1β release through activation of caspase-1 (32, 33). It is noteworthy that the pathological features associated with LT-induced lethality in mice are also quite different from those seen in *B. anthracis*-infected mice. LT-injected mice manifest hypoxia-associated liver failure and pleural edema without mounting the massive cytokine response that usually accompanies either Gram-negative or Gram-positive septic shock (34). Hence, LT alone does not account for the inflammatory cytokine response that accompanies *B. anthracis* infections.

We have now defined a minimal set of three anthrax proteins (ALO, LF, and PA) that can trigger macrophage apoptosis.

The cholesterol-dependent cytolysin *B. anthracis*, anthrolysin O (ALO) was first identified as a TLR4 agonist.

In these experiments, *B. anthracis* cell wall preparations and culture supernatants were first tested for their ability to stimulate TNF-alpha gene expression and induce apoptosis of bone marrow-derived macrophages (BMDMs) in the presence of the p38 inhibitor SB202190. Treatment of BMDMs with a crude, commercially available, *B. anthracis* cell wall preparation did not strongly induce TNF-alpha mRNA expression or apoptosis. In contrast, the *B. anthracis* culture supernatant induced both TNF-alpha mRNA and apoptosis under the same conditions. The TNF-alpha- and apoptosis-inducing activity in the culture supernatant was sensitive to proteinase K digestion, indicating that a proteinaceous component is responsible for both activities. As only TLR4 agonists, but not agonists for other TLRs, can strongly potentiate macrophage apoptosis in the presence of SB202190 (Park et al. Science 2002 297:2048-2051; Hsu et al. Nature 2004 428:341-345), this protein component was expected to act as a TLR4 agonist.

To identify this protein, the *B. anthracis* culture supernatant was sequentially purified through DEAE-Sepharose, Mono S, and phenyl-Sepharose chromatography columns. On the phenyl-Sepharose column, the TNF-alpha- and apoptosis-inducing activities cofractionated as a single peak centered at fraction 26. Analysis of the protein composition of the different column fractions revealed that a 63-kDa polypeptide copurified with both activities. Among the numerous secreted proteins predicted by the *B. anthracis* genome sequence to be present was anthrolysin O, a cholesterol-dependent cytolysin (CDC) encoded by the BA3355 gene (Shannon et al. Infect. Immun. 2003 71:3183-3189). The anthrolysin O polypeptide consists of 512 amino acids with the N-terminal 35 residues coding for a signal peptide, a size consistent with the 63-kDa band described above.

The phenyl-Sepharose fractions were thus analyzed by immunoblotting with anti-anthrolysin O antibody. It was found that anthrolysin O indeed co-purified with the 63-kDa protein, as well as the macrophage-stimulating and apoptosis-inducing activities.

As we identified ALO as a TLR4 agonist that can lead to macrophage apoptosis under conditions of SB202190 pretreatment, we then determined if can also act together with *B. anthracis* LF to induce macrophage apoptosis. To this end, we used ALO, LF, and PA. The three *B. anthracis* proteins were produced in *E. coli* and purified to apparent homogeneity. Addition of ALO, LF and PA to BMDMs induced apoptosis of the latter as shown by either TUNEL assay or Annexin V staining. Each of the three proteins was indispensable for induction of macrophage apoptosis.

In a separate experiment, different amounts of ALO were combined with fixed amounts of LF and PA and the mixture was added to BMDMs. Under these conditions, ALO induced macrophage apoptosis in a dose-dependent manner, but even at the highest concentration tested did not induce apoptosis on its own. This shows that the ability to induce macrophage apoptosis does not represent a nonspecific cytotoxic activity of ALO.

As ALO induces expression of proinflammatory genes by macrophages, the observed apoptotic response may represent a secondary response induced by one of these proinflammatory cytokines, such as TNF-α. To address this issue, we tested BMDMs harboring mutations in genes encoding different pro-apoptotic cytokine receptors for their response to ALO and SB202190. BMDMs from mice homozygous for deletions or inactivating mutations in the genes for TNF receptor 1, Fas, and the type I interferon (IFN) receptor (IFNR1) underwent apoptosis after treatment with ALO and SB202190, just like wild type BMDMs. Only TLR4 mutant BMDMs were resistant to the apoptotic effect of ALO and SB202190.

We next examined the contribution of ALO to macrophage apoptosis caused by infection with live *B. anthracis* (12). BMDMs infected with the wild type Sterne strain of *B. anthracis* underwent apoptosis detected by staining with Hoechst 33258 or by a TUNEL assay. By contrast, macrophages infected with the same multiplicity of infection (MOI) of an ALO-deficient mutant derived from the Sterne strain (13) exhibited a considerably reduced apoptotic response. The inability of the Δalo mutant to induce macrophage apoptosis was rescued by transformation with a plasmid containing the alo gene (13). These results indicate that ALO is necessary for the ability of *B. anthracis* to induce macrophage apoptosis.

Further, a critical interplay between ALO and LT in modulating innate immune responses and inducing macrophage apoptosis was observed.

This interaction between ALO and LT provides new insights to the development of effective strategies for fighting inhalation anthrax, which may improve the current therapeutic scheme based on the use of antibiotics (41). For example, LLO is a major target antigen of antilisterial immunity (42, 43) and protective immunity to *L. monocytogenes* can be induced by either an adoptive transfer of LLO-reactive cytotoxic T lymphocytes (44) or immunization with LLO-derived antigens (45, 46). Similarly, based upon the experiments described herein, it is expected that an ALO-directed vaccination will be useful in the prophylaxis of inhalation anthrax. We believe that ALO, as well as the interaction of LT and ALO, represent important targets for both the development of vaccines and the design of anti-toxin therapies effective for preventing and treating anthrax diseases.

Thus, the present invention relates to compositions for treating or preventing anthrax diseases. Such compositions comprise a compound which modulates, or more preferably inhibits the interaction of lethal factor and anthrolysin O. By "interaction" as used herein, it is meant to include direct interactions, e.g. wherein lethal factor binds to anthrolysin O, as well as indirect interactions, e.g. wherein anthrolysin and lethal factor work in concert through different cell signalling pathways to modulate cellular apoptosis.

In one embodiment, the composition may comprise an isolated ALO protein or a fragment thereof or a mimetic of this protein or fragment thereof or an isolated LT proteins or a fragment thereof or a mimetic of this protein or fragment thereof which inhibits the interaction of ALO and LT. Alternatively, the composition may be incorporated into a vaccination strategy wherein an antibody against ALO or an antigenic region of ALO which invokes an immune response and production of antibodies to ALO in a host is administered to the host. Similar vaccination strategies can be developed with an antibody against LT or an antigenic region of LT. Antibodies specific to ALO or LT will also prevent the interaction of ALO and LT required for macrophage apoptosis.

Such compositions may further comprise acceptable carriers or vehicles for administration to a subject. In a vaccination strategy the composition may further comprise an adjuvant to enhance immunogenicity of the antigen administered to the host.

By "mimetic" as used herein it is meant to include both peptidomimetics and small organic molecules that interact with LT or ALO in similar fashion to the ALO or LT proteins, but which inhibit macrophage apoptosis which occurs upon interaction of LT and ALO in anthrax diseases.

The present invention also relates to methods for identifying compounds for treatment and prevention of anthrax diseases. In these methods, the ability of a compound to modulate the interaction of lethal factor and anthrolysin O is assessed. It is expected that compounds that inhibit the interaction of lethal factor and anthrolysin O thereby inhibiting macrophage apoptosis will be useful in treating and/or preventing anthrax diseases.

Accordingly, the present invention also relates to methods for treating and/or preventing anthrax diseases in a host by administering to host a compound as described herein which modulates, or more preferably inhibits, the interaction of lethal factor and anthrolysin O.

By "host" as used herein it is meant to include any animal infected by anthrax including, but in no way limited to, humans.

The following non limiting examples are provided to further illustrate the present invention.

EXAMPLES

Example 1

Mice and Macrophages

C57BL/6J, C3H/OuJ, C3H/HeJ, B6.MRL-Tnfrsf6$^{lpr}$/J (Fas$^{lpr/lpr}$) and C57BL/6-Tnfrsf1a$^{tm1Imx}$ (TNFR1$^{-/-}$) mice were obtained from the Jackson Laboratory. IFNR1$^{-/-}$ mice in the 129/SvEv background were obtained from Dr. E. Raz (University of California, San Diego). BMDMs were prepared as described previously (11).

Example 2

Reagents

B. anthracis cell walls were purchased from List Biological Laboratories, Inc. Other reagents used for treatment of BMDMs included: LPS (E. coli; Sigma), peptidoglycan (Fluka), poly(I-C) (Amersham Biosciences), CpG oligodeoxynucleotide (TIB MOLBIOL), Pam$_3$CSK$_4$ (EMC Microcollections), and R-848 (GLS Synthesis). SB202190 was from Calbiochem.

Example 3

Bacterial Strains, Culture and Infection

B. anthracis Sterne strain 7702 and its derivatives were described previously (13). Bacteria were grown in brain heart infusion broth (BHI; Difco), without added bicarbonate, with shaking (200 rpm) at 37° C. in an air shaker incubator or on BHI agar in a humidified incubator. Bacterial infection of macrophage cultures was described previously (12).

Example 4

Purification of ALO from Bacterial Culture Supernatants

All buffers used in dialysis and column chromatography were prepared with double-distilled and autoclaved water and contained protease inhibitors (10 µM phenylmethylsulfonyl fluoride, 20 nM pepstatin A, 6 nM leupeptin, and 20 µM bisbenzamidine). The buffers were confirmed to be endotoxin-free by testing their ability to induce TNF-expression in macrophages. To purify macrophage-stimulating activity from B. anthracis culture supernatants, bacteria were grown in BHI broth until OD595 reached 1.0. After removing bacteria by centrifugation, the supernatant (2 liters) was filtered through a 0.2 µm-pore Nylon filters (Nalgene), concentrated up to 80-fold on a Centricon Plus-20 Filter Device (Millipore), and dialyzed in buffer D100 (20 mM Tris-Cl [pH 7.0], 100 mM NaCl, and 0.1 mM EDTA). Proteins (84 mg) in the culture concentrate were applied to a DEAE-Sepharose column (10 ml) equilibrated with buffer D100. The macrophage-stimulating activity was found to pass through this column under this particular loading condition. Proteins in the flow-through fraction (61 mg) were equilibrated in buffer S50 (20 mM HEPES-KOH [pH7.0], 50 mM NaCl, and 0.1 mM EDTA) by dialysis and applied to a Mono S column (1 ml per 20 mg protein) equilibrated with buffer S50. After washing with buffer S50, bound proteins were eluted with a linear gradient of 50 to 1000 mM NaCl. The major peak fractions of macrophage-stimulating activity (3.1 mg) were pooled and mixed with an equal volume of 100 mM Tris-Cl (pH 7.0) and 3 M $(NH_4)_2SO_4$, and applied to a phenyl-Sepharose column (0.5 ml) equilibrated with buffer P1500 (50 mM $Na_2HPO_4$ [pH 7.0], 1.5 M $(NH_4)_2SO_4$, and 0.1 mM EDTA). After washing with buffer P1500, bound proteins were eluted with an inverse linear gradient of 1.5 to 0 M $(NH_4)_2SO_4$. The phenyl-Sepharose fractions active in macrophage stimulation were stored at 80° C.

Example 5

Preparation of Recombinant Proteins

Recombinant LF, PA and CDCs were expressed in and purified from *E. coli* strain BL21 (DE3) bearing the appropriate plasmid construct as described previously (13-15). The analyses of macrophages activation by CDCs were performed with proteins synthesized in reticulocyte lysates using T7 expression plasmids harboring a CDC gene and the TNT T7 kit (Promega).

Example 6

Protein Analysis

Whole-cell extracts for immunoblot analysis were prepared with lysis buffer (20 mM HEPES-KOH at pH 7.6, 150 mM NaCl, 10% glycerol, 1% Triton X-100, 25 mM β-glycerophosphate, 2 mM EDTA, and protease inhibitors) and subjected to SDS-PAGE. Proteins transferred to nitrocellulose membrane were probed with rabbit antiserum against recombinant ALO (13), and antibodies directed against actin (Sigma), iNOS, phospho-p38a, p38a, and IκBα (all from Santa Cruz Biotechnology), and the immune complexes were visualized with the ECL Western blot reagent (Pierce). TNF-α secretion was measured by an ELISA (R&D Systems).

Example 7

RNA Analysis

Total RNA was isolated using the RNAwiz reagent (Ambion). For realtime PCR analysis, cDNAs were synthesized with the Superscript II reverse transcriptase system (Invitrogen). An amount of cDNA equivalent to 0.2 μg of total RNA was subjected to 40 cycles of amplification consisting of a 15-sec incubation at 95° C. and a 1 min incubation at 60° C. Output was monitored using SYBR Green core reagents and the ABI Prism 7700 System (PE Applied Biosystems). The results were normalized to the level of cyclophilin mRNA. Individual primer sequences are available upon request.

Example 8

Measurement of Cell Viability and Hemolysis

TUNEL assay and Hoechst staining were performed as described (11). MTT assay and Annexin V staining were carried out using an MTT kit and Annexin V-Alexa568, respectively, according to manufacturer's (Roche) instruction. The hemolysis assay was performed by incubating mouse erythrocytes (whole blood diluted 10-fold with phosphate-buffered saline) with CDCs for 30 min at 37° C., centrifuging the mixture at 8000×g for 1 min, and measuring A350 of the supernatant. The relative optical density was compared to that of erythrocytes treated with 0.1% Triton X-100 and used to determine % hemolysis.

Example 9

Immunodepletion of ALO 0.4 ml of culture supernatants were mixed with 5 μl of ALO-specific antiserum on a rotating wheel for 12 hrs at 4° C. 50 μl of Protein A-agarose beads were then added and incubated for 1 hr. Samples were briefly centrifuged to precipitate the beads and supernatants were collected for further analyses.

REFERENCES

1. Dixon, T. C., M. Meselson, J. Guillemin, and P. C. Hanna. 1999. Anthrax. N. Engl. J. Med. 341: 815-826.
2. Collier, R. J., and J. A. Young. 2003. Anthrax toxin. Annu. Rev. Cell Dev. Biol. 19: 4570.
3. Moayeri, M., and S. H. Leppla. 2004. The roles of anthrax toxin in pathogenesis. Curr. Opin. Microbiol. 7: 19-24.
4. Bradley, K. A., J. Mogridge, M. Mourez, R. J. Collier, and J. A. Young. 2001. Identification of the cellular receptor for anthrax toxin. Nature. 414: 225-229.
5. Scobie, H. M., G. J. Rainey, K. A. Bradley, and J. A. Young. 2003. Human capillary morphogenesis protein 2 functions as an anthrax toxin receptor. Proc. Natl. Acad. Sci. U.S.A. 100: 5170-5174.
6. Leppla, S. H. 1982. Anthrax toxin edema factor: a bacterial adenylate cyclase that increases cyclic AMP concentrations of eukaryotic cells. Proc. Natl. Acad. Sci. U.S.A. 79: 3162-3166.
7. Klimpel, K. R., N. Arora, and S. H. Leppla. 1994. Anthrax toxin lethal factor contains a zinc metalloprotease consensus sequence which is required for lethal toxin activity. Mol. Microbiol. 13: 1093-1100.
8. Duesbery, N. S., C. P. Webb, S. H. Leppla, V. M. Gordon, K. R. Klimpel, T. D. Copeland, N. G. Ahn, M. K. Oskarsson, K. Fukasawa, K. D. Paull, and G. F. Vande Woude. 1998. Proteolytic inactivation of MAP-kinase-kinase by anthrax lethal factor. Science. 280: 734-737.
9. Vitale, G., R. Pellizzari, C. Recchi, G. Napolitani, M. Mock, and C. Montecucco. 1998. Anthrax lethal factor cleaves the N-terminus of MAPKKs and induces tyrosine/threonine phosphorylation of MAPKs in cultured macrophages. Biochem. Biophys. Res. Commun. 248: 706-711.
10. Xia, Y., Z. Wu, B. Su, B. Murray, and M. Karin. 1998. JNKK1 organizes a MAP kinase module through specific and sequential interactions with upstream and downstream components mediated by its amino-terminal extension. Genes. Dev. 12: 3369-3381.
11. Park, J. M., F. R. Greten, Z. W. Li, and M. Karin M. 2002. Macrophage apoptosis by anthrax lethal factor through p38 MAP kinase inhibition. Science. 297: 2048-2051.
12. Hsu, L. C., J. M. Park, K. Zhang, J. L. Luo, S. Maeda, R. J. Kaufman, L. Eckmann, D. G. Guiney, and M. Karin. 2004. The protein kinase PKR is required for macrophage apoptosis after activation of Toll-like receptor 4. Nature. 428: 341-345.
13. Shannon, J. G., C. L. Ross, T. M. Koehler, and R. F. Rest. 2003. Characterization of anthrolysin O, the *Bacillus anthracis* cholesterol-dependent cytolysin. Infect. Immun. 71: 3183-3189.
14. Cunningham, K., D. B. Lacy, J. Mogridge, R. J. Collier. 1998. Characterization of membrane translocation by anthrax protective antigen. Biochemistry. 37: 15737-15746.
15. Shepard, L. A., A. P. Heuck, B. D. Hamman, J. Rossjohn, M. W. Parker, K. R. Ryan, A. E. Johnson, and R. K. Tweten. 1998. Identification of a membrane-spanning domain of the thiol-activated pore-forming toxin *Clostridium perfringens* perfringolysin O: an alpha-helical to beta-sheet transition identified by fluorescence spectroscopy. Biochemistry. 37: 14563-14574.
16. Read, T. D., S. N. Peterson, N. Tourasse, L. W. Baillie, I. T. Paulsen, K. E. Nelson, H. Tettelin, D. E. Fouts, J. A. Eisen, S. R. Gill, E. K. Holtzapple, O. A. Okstad, E. Helgason, J. Rilstone, M. Wu, J. F. Kolonay, M. J. Beanan, R. J. Dodson, L. M. Brinkac, M. Gwinn, R. T. DeBoy, R. Madpu, S. C. Daugherty, A. S. Durkin, D. H. Haft, W. C. Nelson, J. D. Peterson, M. Pop, H. M. Khouri, D. Radune, J. L. Benton, Y. Mahamoud, L. Jiang, I. R. Hance, J. F. Weidman, K. J. Berry, R. D. Plaut, A. M. Wolf, K. L. Watkins, W. C. Nierman, A. Hazen, R. Cline, C. Redmond, J. E. Thwaite, O. White, S. L. Salzberg, B. Thomason, A. M. Friedlander, T. M. Koehler, P. C. Hanna, A. B. Kolsto, and C. M. Fraser. 2003. The genome sequence of *Bacillus anthracis* Ames and comparison to closely related bacteria. Nature. 423: 81-86.
17. Malley, R., P. Henneke, S. C. Morse, M. J. Cieslewicz, M. Lipsitch, C. M. Thompson, E. Kurt-Jones, J. C. Paton, M. R. Wessels, and D. T. Golenbock. 2003. Recognition of pneumolysin by Toll-like receptor 4 confers resistance to pneumococcal infection. Proc. Natl. Acad. Sci. U.S.A. 100: 1966-1971.
18. Ulevitch, R. J., and P. S. Tobias. 1995. Receptor-dependent mechanisms of cell stimulation by bacterial endotoxin. Annu. Rev. Immunol. 13: 437-457.
19. Seong, S. Y., and P. Matzinger. 2004. Hydrophobicity: an ancient damage-associated molecular pattern that initiates innate immune responses. Nat. Rev. Immunol. 4: 469-478.
20. Tweten, R. K., Parker, M. W., and A. E. Johnson. 2001. The cholesterol-dependent cytolysins. Curr. Top. Microbiol. Immunol. 257: 15.33.
21. Dempsey, C. E. 1990. The actions of melittin on membranes. Biochim. Biophys. Acta. 1031:143-161.
22. Tsukada, H., I. Kawamura, T. Fujimura, K. Igarashi, M. Arakawa, and M. Mitsuyama. 1992. Induction of macrophage interleukin-1 production by *Listeria monocytogenes* hemolysin. Cell. Immunol. 140: 21-30.
23. Stassen, M., C. Muller, C. Richter, C. Neudorfl, L. Hultner, S. Bhakdi, I. Walev, and E. Schmitt. 2003. The streptococcal exotoxin streptolysin O activates mast cells to produce tumor necrosis factor a by p38 mitogen-activated protein kinase- and protein kinase C-dependent pathways. Infect. Immun. 71: 6171-6177.
24. Kopp, E., and R. Medzhitov. 2003. Recognition of microbial infection by Toll-like receptors. Curr. Opin. Immunol. 15: 396-401.
25. Beutler, B., and E. T. Rietschel. 2003. Innate immune sensing and its roots: the story of endotoxin. Nat. Rev. Immunol. 3:169-176.
26. Cohen, J. 2002. The immunopathogenesis of sepsis. Nature. 420: 885-891.
27. Popov, S. G., T. G. Popova, E. Grene, F. Klotz, J. Cardwell, C. Bradburne, Y. Jama, M. Maland, J. Wells, A. Nalca, T. Voss, C. Bailey, and K. Alibek. 2004. Systemic cytokine response in murine anthrax. Cell. Microbiol. 6: 225-233.
28. Pickering, A. K., and T. J. Merkel. 2004. Macrophages release tumor necrosis factor alpha and interleukin-12 in response to intracellular *Bacillus anthracis* spores. Infect. Immun. 72: 3069-3072.
29. Hanna, P. C., D. Acosta, and R. J. Collier. 1993. On the role of macrophages in anthrax. Proc. Natl. Acad. Sci. U.S.A. 90: 10198-10201.

30. Erwin, J. L., L. M. DaSilva, S. Bavari, S. F. Little, A. M. Friedlander, and T. C. Chanh. 2001. Macrophage-derived cell lines do not express proinflammatory cytokines after exposure to *Bacillus anthracis* lethal toxin. Infect. Immun. 69: 1175-1177.

31. Cordoba-Rodriguez, R., H. Fang, C. S. Lankford, and D. M. Frucht. 2004. Anthrax lethal toxin rapidly activates caspase-1/ICE and induces extracellular release of interleukin (IL)-1beta and IL-18. J. Biol. Chem. 279: 20563-20566.

32. Chen, Y., M. R. Smith, K. Thirumalai, and A. Zychlinsky. 1996. A bacterial invasin induces macrophage apoptosis by binding directly to ICE. EMBO J. 15: 3853-3860.

33. Hersh, D., D. M. Monack, M. R. Smith, N. Ghori, S. Falkow, and A. Zychlinsky. 1999. The *Salmonella* invasin SipB induces macrophage apoptosis by binding to caspase-1. Proc. Natl. Acad. Sci. U.S.A. 96: 2396-2401.

34. Moayeri, M., D. Haines, H. A. Young, and S. H. Leppla. 2003. *Bacillus anthracis* lethal toxin induces TNF-alpha-independent hypoxia-mediated toxicity in mice. J. Clin. Invest. 112: 670-682.

35. Portnoy, D. A., T. Chakraborty, W. Goebel, P. Cossart. 1992. Molecular determinants of *Listeria monocytogenes* pathogenesis. Infect. Immun. 60: 1263-1267.

36. Paton, J. C. 1996. The contribution of pneumolysin to the pathogenicity of *Streptococcus pneumoniae*. Trends Microbiol. 4: 103-106.

37. Rood, J. I. 1998. Virulence genes of *Clostridium perfringens*. Annu. Rev. Microbiol. 52: 333-360.

38. Decatur, A. L., and D. A. Portnoy. 2000. A PEST-like sequence in listeriolysin O essential for *Listeria monocytogenes* pathogenicity. Science. 290: 992-995.

39. Madden, J. C., N. Ruiz, M. Caparon. 2001. Cytolysin-mediated translocation (CMT): a functional equivalent of type III secretion in Gram-positive bacteria. Cell 104:143-152.

40. Meehl, M. A., and M. G. Caparon. 2004. Specificity of streptolysin O in cytolysinmediated translocation. Mol. Microbiol. 52: 1665-1676.

41. Gilligan, P. H. 2002. Therapeutic challenges posed by bacterial bioterrorism threats. Curr. Opin. Microbiol. 5: 489-495.

42. Pamer, E. G., J. T. Harty, and M. J. Bevan. 1991. Precise prediction of a dominant class I MHC-restricted epitope of *Listeria monocytogenes*. Nature. 353: 852-855.

43. Bouwer, H. G., C. S. Nelson, B. L. Gibbins, D. A. Portnoy, and D. J. Hinrichs. 1992. Listeriolysin O is a target of the immune response to *Listeria monocytogenes*. J Exp Med. 175:1467-1471.

44. Harty, J. T., and M. J. Bevan. 1992. CD8+ T cells specific for a single nonamer epitope of *Listeria monocytogenes* are protective in vivo. J. Exp. Med. 175: 1531-1538.

45. Sirard, J. C., C. Fayolle, de Chastellier, M. Mock, C. Leclerc, and P. Berche. 1997. Intracytoplasmic delivery of listeriolysin O by a vaccinal strain of *Bacillus anthracis* induces CD8-mediated protection against *Listeria monocytogenes*. J. Immunol. 159:4435-4443.

46. Cornell, K. A., H. G. Bouwer, D. J. Hinrichs, and R. A. Barry. 1999. Genetic immunization of mice against *Listeria monocytogenes* using plasmid DNA encoding listeriolysin O. J. Immunol. 163: 322-329.

What is claimed is:

1. A method of identifying potential compounds for inhibiting macrophage apoptosis which occurs upon interaction of lethal factor and anthrolysin O in anthrax disease comprising:
   providing macrophages;
   providing purified lethal factor and purified anthrolysin O;
   providing a compound to be tested;
   combining the macrophages, purified lethal factor, and purified anthrolysin O;
   measuring apoptosis of macrophages in a sample in the presence of the compound;
   measuring apoptosis of macrophages in a sample without the compound; and
   comparing apoptosis of the macrophages in the sample without the compound and the sample with the compound, wherein apoptosis is measured by Hoechst staining or by a TUNEL assay.

* * * * *